United States Patent
Shinohara et al.

(10) Patent No.: US 11,832,942 B2
(45) Date of Patent: Dec. 5, 2023

(54) BIOLOGICAL MATERIAL MEASURING APPARATUS

(71) Applicant: Mitsubishi Electric Corporation, Tokyo (JP)

(72) Inventors: Kosuke Shinohara, Tokyo (JP); Kentaro Enoki, Tokyo (JP); Koichi Akiyama, Tokyo (JP); Shimpei Ogawa, Tokyo (JP); Daisuke Fujisawa, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 709 days.

(21) Appl. No.: 16/962,229

(22) PCT Filed: Feb. 2, 2018

(86) PCT No.: PCT/JP2018/003528
§ 371 (c)(1),
(2) Date: Jul. 15, 2020

(87) PCT Pub. No.: WO2019/150543
PCT Pub. Date: Aug. 8, 2019

(65) Prior Publication Data
US 2021/0059574 A1    Mar. 4, 2021

(51) Int. Cl.
*A61B 5/1455* (2006.01)
*G01N 21/359* (2014.01)
*G01N 21/41* (2006.01)

(52) U.S. Cl.
CPC ......... *A61B 5/1455* (2013.01); *G01N 21/359* (2013.01); *G01N 21/41* (2013.01)

(58) Field of Classification Search
CPC .............. A61B 5/1455; A61B 5/14551; A61B 5/14552; A61B 5/14532; G01N 21/35; G01N 21/359; G01N 21/41; G01N 21/552

See application file for complete search history.

(56) References Cited

U.S. PATENT DOCUMENTS

| | | | |
|---|---|---|---|
| 4,830,502 A | 5/1989 | Saito et al. | |
| 4,896,952 A * | 1/1990 | Rosenbluth | G02B 17/08 359/638 |

(Continued)

FOREIGN PATENT DOCUMENTS

| | | |
|---|---|---|
| CN | 1536347 A | 10/2004 |
| CN | 101043844 A | 9/2007 |

(Continued)

OTHER PUBLICATIONS

International Search Report and Written Opinion dated May 1, 2018 for PCT/JP2018/003528 filed on Feb. 2, 2018, 14 pages including English Translation of the International Search Report.

(Continued)

*Primary Examiner* — Chu Chuan Liu
(74) *Attorney, Agent, or Firm* — XSENSUS LLP

(57) ABSTRACT

A biological material measuring apparatus includes an infrared light source unit to radiate infrared light in entirety or part of a wavelength region including absorption wavelengths of a biological material, a prism to cause the infrared light radiated from the infrared light source unit to pass therethrough and emit the infrared light to a living body surface while being in contact with the living body surface, a light source to radiate light of a wavelength in a visible light region or a near infrared region to the prism, and a light (Continued)

position detector to detect a path of light from the light source by detecting light from the light source which is emitted from the prism.

14 Claims, 10 Drawing Sheets

(56) References Cited

U.S. PATENT DOCUMENTS

| | | |
|---|---|---|
| 2004/0199060 A1 | 10/2004 | Oshima et al. |
| 2006/0063988 A1 | 3/2006 | Schurman et al. |
| 2009/0059226 A1 | 3/2009 | Kajiki et al. |
| 2015/0265190 A1 | 9/2015 | Ikebe |
| 2016/0198985 A1 | 7/2016 | Park et al. |
| 2017/0143210 A1 | 5/2017 | Ikebe |
| 2017/0146455 A1 | 5/2017 | Mäntele et al. |
| 2018/0067041 A1 | 3/2018 | Ogawa et al. |
| 2021/0109019 A1* | 4/2021 | Bauer ............... A61B 5/4839 |

FOREIGN PATENT DOCUMENTS

| | | |
|---|---|---|
| CN | 106535760 A | 3/2017 |
| CN | 107430028 A | 12/2017 |
| JP | 61-122545 A | 6/1986 |
| JP | 2003-042952 A | 2/2003 |
| JP | 2004-329888 A | 11/2004 |
| JP | 2004-340797 A | 12/2004 |
| JP | 2005-073763 A | 3/2005 |
| JP | 2009-075073 A | 4/2009 |
| JP | 2015-173935 A | 10/2015 |
| JP | 2015-198689 A | 11/2015 |

OTHER PUBLICATIONS

Office Action dated Feb. 2, 2023 in Chinese Patent Application No. 201880088004.6 with computer-generated English translation, 29 pages.

Office Action dated Aug. 26, 2021, in corresponding Indian Patent Application No. 202027029082, 5 pages.

Chinese Office Action dated Jul. 7, 2023, in corresponding Chinese Application No. 201880088004.6, 39pp.

* cited by examiner

BIOLOGICAL MATERIAL MEASURING APPARATUS

CROSS-REFERENCE TO RELATED APPLICATION

The present application is based on PCT filing PCT/JP2018/003528, filed Feb. 2, 2018, the entire contents of which are incorporated herein by reference.

TECHNICAL FIELD

The present invention relates to biological material measuring apparatuses, and more particularly, to a biological material measuring apparatus that uses infrared light to measure a biological material such as sugar in a living body.

BACKGROUND ART

A conventional invasive sensor draws blood with a needle and analyzes a component of a material in a living body. In particular, for blood sugar level sensors commonly used, a non-invasive type is desired to alleviate patient's pain caused by puncture. Although one type of non-invasive blood sugar level sensor using infrared light is capable of directly detecting a fingerprint spectrum of sugar, infrared light cannot reach a deep portion from a skin surface because infrared light is absorbed well by water. Under the circumstances, such a technique is demanded that detects a blood sugar level stably with high accuracy even when absorption by sugar in a living body is little.

In response to such a demand, for example, the apparatus described in in PTL 1 measures a blood sugar level by the attenuated total reflection (ATR) method.

CITATION LIST

Patent Literature

PTL 1: Japanese Patent Laying-Open No. 2003-42952

SUMMARY OF INVENTION

Technical Problem

According to PTL 1, a wavelength tunable laser is used because measurements performed at a plurality of wavelengths are necessary for improved accuracy of measurement. The wavelength tunable laser is, however, implemented as an external resonator, leading to large size and high cost.

An object of the present invention is therefore to provide a biological material measuring apparatus capable of measuring an amount of a biological material at low cost.

Solution to Problem

A biological material measuring apparatus according to a first aspect of the present invention includes an infrared light source unit to radiate infrared light in entirety or part of a wavelength region including absorption wavelengths of a biological material, a prism to cause the infrared light radiated from the infrared light source unit to pass therethrough and emit the infrared light to a living body surface while being in contact with the living body surface, a light source to radiate light of a wavelength in a visible light region or a near infrared region to the prism, and a light position detector to detect a path of light from the light source by detecting light from the light source which is emitted from the prism.

A biological material measuring apparatus according to a second aspect of the present invention includes an ATR prism adherable to a living body surface, an infrared light source unit to radiate, to the ATR prism, infrared light in entirety or part of a wavelength region including absorption wavelengths of a biological material, and an infrared photodetector to detect infrared light of at least one wavelength which is emitted from the ATR prism.

A biological material measuring apparatus according to a third aspect of the present invention includes an ATR prism adherable to a living body surface, an infrared light source unit to radiate, to the ATR prism, infrared light in entirety or part of a wavelength region including absorption wavelengths of a biological material, and an infrared photodetector to detect infrared light emitted from the ATR prism. The infrared light source unit comprises a plurality of light sources, each of which radiates infrared light of a single wavelength included in a wavelength region detectable by the infrared photodetector.

Advantageous Effects of Invention

The present invention eliminates the need for a wavelength tunable laser, and thus, can measure an amount of a biological material present in a surface of a living body at low cost.

DESCRIPTION OF EMBODIMENTS

Embodiments of the present invention will now be described with reference to the drawings.

Embodiment 1

Although description will be given below by taking a blood sugar level as an example measuring object, a measuring apparatus of the present invention is applicable to measurement of a blood sugar level, as well as measurement of any other biological material.

In the ATR method described in PTL 1, a prism is brought into contact with a measurement skin, which prevents evanescent light from penetrating deep into the measurement skin. This leads to low measurement accuracy of an amount of a biological material. The present embodiment measures an amount of a biological material without using the ATR method.

Figure 1:
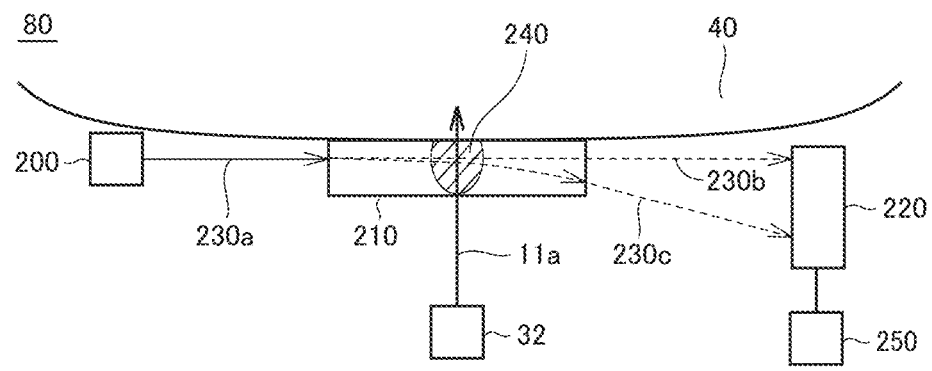
FIG. 1 shows a configuration of a mobile, non-invasive biological material measuring apparatus 80 of Embodiment 1.

FIG. 1 shows a configuration of a mobile, non-invasive biological material measuring apparatus 80 of Embodiment 1.

Non-invasive biological material measuring apparatus 80 includes a light source 200, a prism 210, a light position detector 220, and an infrared light source unit 32.

Infrared light source unit 32 includes at least one or more infrared light sources. Infrared light source unit 32 includes a wideband quantum cascade laser that radiates infrared light in entirety or part of the wavelength region in the wavelength range of 8.5 µm to 10 µm, which includes wavelengths of a finger print spectrum of sugar. The wavelengths for use in measurements are, for example, $\lambda 1$, $\lambda 2$, and $\lambda 3$. Light of $\lambda 1$ and light of $\lambda 2$ are absorbed by a sugar in a human body. Light of $\lambda 3$ is not absorbed by sugar in a human body and is used as a reference wavelength. The wavelengths for use in measurements may be four wavelengths further including $\lambda 4$.

Infrared light radiated from infrared light source unit 32 passes through prism 210 as incident infrared light 11a and enters a living body surface 40, which is a subject's skin.

Prism 210 is made of a material such as zinc sulfide (ZnS) which is highly transparent in a wavelength region of visible light to a wavelength region of infrared light.

Light source 200 is a laser that outputs light of one wavelength in the wavelength region of visible light to a wavelength region of near infrared. Light output from light source 200 enters prism 210 as incident light 230a, passes through prism 210, and is then radiated from prism 210 as radiated light 230b or radiated and refracted light 230c. A difference between radiated light 230b and radiated and refracted light 230c arises from the change of state within the prism, which will be described below. Radiated light 230b or radiated and refracted light 230c enters light position detector 220.

Light position detector 220 detects a path of light from light source 200 by detecting the light from light source 200 which is emitted from prism 210. Light position detector 220 includes a photodetector capable of detecting radiated light 230b or radiated and refracted light 230c. Light position detector 220 detects a position at which light enters the photodetector. The material for light position detector 220 may be, for example, an inexpensive photodiode or a plasmon with excellent wavelength selectivity.

Next, an operation of measuring a blood sugar level in the present embodiment will be described.

A state in which the light output from infrared light source unit 32 is zero is referred to as a reference state. In the reference state, the state inside prism 210 is uniform, and accordingly, light output from light source 200 is refracted only when entering prism 210 and when exiting the prism. In the reference state, the position at which radiated light 230b enters light position detector 220 is referred to as a reference position.

Then, infrared light source unit 32 outputs infrared light of a fingerprint spectrum wavelength of sugar as incident infrared light 11a. Incident infrared light 11a enters living body surface 40 of the subject through prism 210. Infrared light is absorbed by the sugar present in living body surface 40 of the subject. Absorption heat is generated in living body surface 40 due to the absorption. The generated absorption heat is conducted to prism 210, causing a temperature gradient inside prism 210, which forms a refractive index gradient 240 in accordance with the temperature gradient. This is because a refractive index changes as temperature changes. This state is referred to as state 1.

In state 1, incident light 230a passes through refractive index gradient 240. Incident light 230a is refracted in accordance with a refractive index at a position in refractive index gradient 240 through which light passes.

The refracted incident light 230a is radiated from prism 210 as radiated and refracted light 230c and enters light position detector 220. In state 1, the position at which radiated light 230b enters light position detector 220 is referred to as a displacement position.

A controller 250 measures an amount of the sugar in living body surface 40 based on a difference between the position of incidence of radiated light 230b which is detected by light position detector 220 in the reference state in which the infrared light source unit does not emit infrared light and the position of incidence of radiated and refracted light 230c which is detected by light position detector 220 in state 1 in which the infrared light source unit emits infrared light.

An effect of noise can be eliminated through the above operation performed at wavelengths $\lambda 1$ and $\lambda 2$ at which light is absorbed by the sugar in a human body and at $\lambda 3$ at which light is not absorbed, enabling more accurate calculation of a blood sugar level.

When a plasmon is used as light position detector 220, the wavelength selectivity thereof allows calculation of a displacement position at each of $\lambda 1$, $\lambda 2$ and $\lambda 3$, enabling higher-accuracy measurement of a blood sugar level.

Figure 2:
FIG. 2 shows an example use of mobile, non-invasive biological material measuring apparatuses 80 of Embodiments 1 to 6.

FIG. 2 shows an example use of mobile, non-invasive biological material measuring apparatuses 80 of Embodiments 1 to 6. As shown in FIG. 2, the blood sugar level in a living body of a subject is measured with the head of mobile, non-invasive biological material measuring apparatus 80 being brought into contact with a subject's lip with a thin keratin layer. Although a measurement site is desirably a lip with a thin keratin layer, it may be another site. It suffices that the measurement site is other than a site with a thick keratin layer, such as a palm. For example, measurements can also be made on a cheek of a face, an earlobe, or the back of a hand.

[Notes]

The biological material measuring apparatus (80) of Embodiment 1 has the following features.

(1) A biological material measuring apparatus (80) includes an infrared light source unit (32) to radiate infrared light in entirety or part of a wavelength region including absorption wavelengths of a biological material, a prism (210) to cause the infrared light radiated from the infrared light source unit (32) to pass therethrough and emit the infrared light to a living body surface (40) while being in contact with the living body surface, a light source (200) to radiate light of a wavelength in a visible light region or a near infrared region to the prism, and a light position detector (220) to detect a path of light from the light source (200) by detecting light from the light source (200) which is emitted from the prism (210).

With such a configuration, the path of light from the light source (200) is detected, enabling high-accuracy measurement of an amount of a biological material present in the living body surface.

(2) The infrared light emitted to the living body surface (40) is absorbed by the biological material present in the living body surface (40), and the absorption generates absorption heat to form a refractive index gradient (240) in the prism (210).

Such a configuration can generate the refractive index gradient (240) corresponding to the biological material present in the living body surface (40) in the path through which the light radiated from the light source passes.

(3) The light radiated from the light source (200) passes through the refractive index gradient (240) formed in the prism (210) due to the absorption heat of the biological material.

Such a configuration can allow the light radiated from the light source (200) to be refracted at a refractive index corresponding to the amount of the biological material.

(4) The biological material measuring apparatus (80) includes a controller (250) to measure an amount of the biological material based on a difference between a position of incidence of light radiated from the light source (200) which is detected by the light position detector (220) when the infrared light source unit (32) does not radiate the infrared light and a position of incidence of light emitted from the light source (200) which is detected by the light position detector (220) when the infrared light source unit (32) radiates the infrared light.

Such a configuration enables measurement of an amount of a biological material based on a difference in the position of incidence of light radiated from the light source (200) which is detected by the light position detector (220) between when the infrared light source unit (32) does not emit infrared light and when the infrared light source unit (32) emits infrared light.

Embodiment 2

Figure 3:
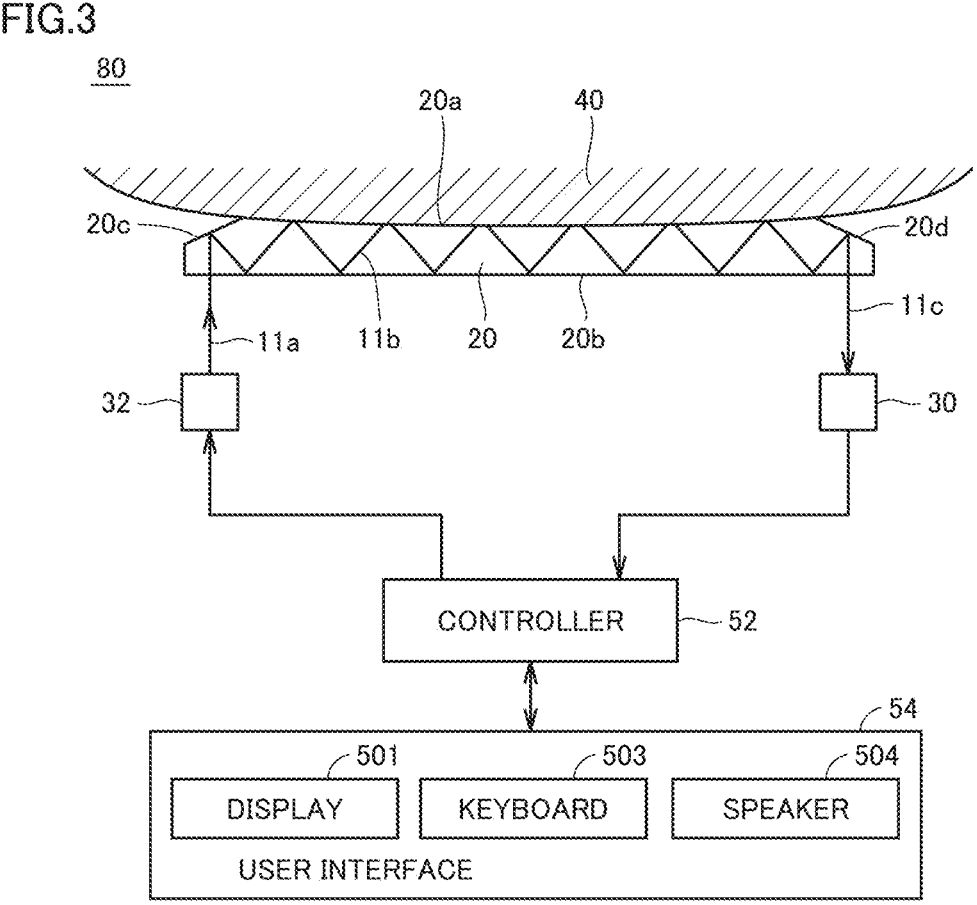
FIG. 3 shows a configuration of mobile, non-invasive biological material measuring apparatus 80 of Embodiment 2.

FIG. 3 shows a configuration of mobile, non-invasive biological material measuring apparatus 80 of Embodiment 2.

Non-invasive biological material measuring apparatus 80 includes an ATR prism 20, an infrared light source unit 32, an infrared photodetector 30, a controller 52, and a user interface 54.

Infrared light source unit 32 includes at least one infrared light source. Infrared light source unit 32 radiates infrared light in entirety or part of a wavelength range with absorption wavelengths of a biological material.

Infrared photodetector 30 detects infrared light emitted from ATR prism 20.

Controller 52 controls infrared light source unit 32 and infrared photodetector 30. Controller 52 calculates the concentration of the blood sugar level of a living body based on the intensity of the infrared light detected by infrared photodetector 30.

User interface 54 includes a display 501, a keyboard 503, and a speaker 504.

ATR prism 20 is mounted in the head of non-invasive biological material measuring apparatus 80. ATR prism 20 is adherable to living body surface 40 of the subject.

Figure 4:
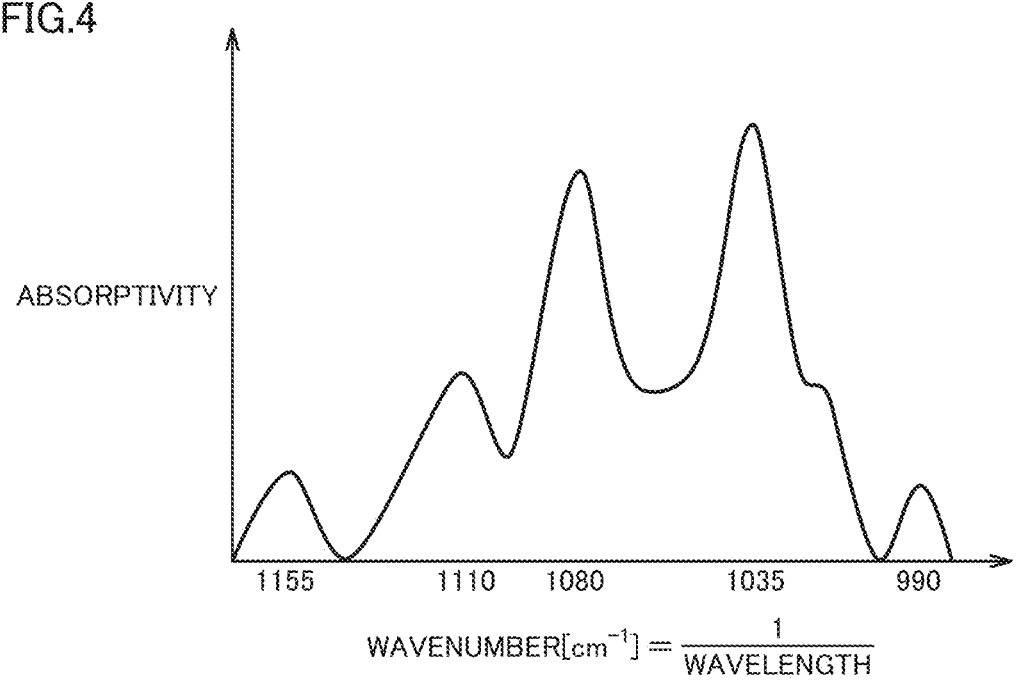
FIG. 4 shows a fingerprint spectrum of sugar.

FIG. 4 shows a fingerprint spectrum of sugar.

As shown in FIG. 3, when biological material measuring apparatus 80 is activated with ATR prism 20 being brought into contact with living body surface 40 of the subject, infrared light source unit 32 radiates infrared light in entirety or part of the wavelength region in the wavelength range of 8.5 µm to 10 µm, which includes a fingerprint spectrum of sugar as shown in FIG. 4.

Incident infrared light 11a emitted from infrared light source unit 32 is reflected at an end face 20c of ATR prism 20 and then turns into propagating infrared light 11b. Propagating infrared light 11b passes through ATR prism 20 being in contact with living body surface 40 while repeating total reflection at end faces 20a and 20b of ATR prism 20. Propagating infrared light 11b that has passed through ATR prism 20 is reflected at an end face 20d of ATR prism 20 and then turns into radiated infrared light 11c. Infrared photodetector 30 detects the intensity of radiated infrared light 11c.

Evanescent light is generated at end face 20a which is the interface between ATR prism 20 and living body surface 40. The evanescent light penetrates living body surface 40 and is absorbed by sugar.

A smaller difference in the refractive index between living body surface 40 and ATR prism 20 results in more intense evanescent light. The evanescent light which has leaked from ATR prism 20 toward living body surface 40 in total reflection of propagating infrared light 11b at end face 20a is absorbed by the biological material in living body surface 40, so that the intensity of the infrared light totally reflected at end face 20a attenuates. A larger amount of biological material accordingly leads to more absorption of evanescent light, resulting in more attenuation of the intensity of the infrared light totally reflected.

A skin is composed of an epidermis near a skin surface and a corium below the epidermis. The epidermis includes a stratum corneum, a stratum granulosum, a stratum spinosum, and a stratum basale in order from the vicinity of the skin surface, the thicknesses of which are 10 µm, about several micrometers, 100 µm, and about several micrometers, respectively. Cells are produced in the stratum basale and stacked on the stratum spinosum. The cells die out in the stratum granulosum because water (interstitial fluid) does not reach the stratum granulosum. The dead cells are hardened in the stratum corneum. Sugar and any other biological material are present in the interstitial fluid of the epidermis. The interstitial fluid increases from the stratum corneum to the stratum spinosum. The intensity of the infrared light totally reflected accordingly changes in accordance with the penetration length of evanescent light. Herein, the penetration length is also referred to as a penetration depth.

Evanescent light attenuates exponentially from the interface toward living body surface 40, and has a penetration length approximately equal to its wavelength. Spectroscopy using ATR prism 20 can thus measure an amount of a biological material in the region up to the penetration length. For example, a fingerprint spectrum of sugar has wavelengths of 8.5 µm to 10 µm, and accordingly, an amount of sugar in the region in such a range from the prism surface of ATR prism 20 can be detected.

Figure 5:
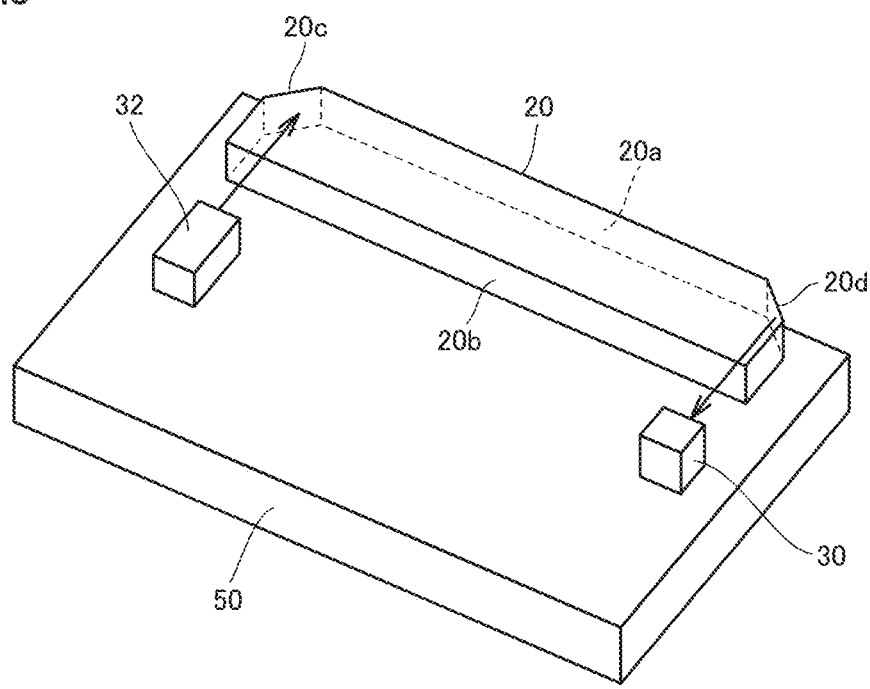
FIG. 5 shows a structure of a head of non-invasive biological material measuring apparatus 80 of Embodiment 2.

FIG. 5 shows a structure of a head of non-invasive biological material measuring apparatus 80 of Embodiment 2. The head is formed of a substrate 50, ATR prism 20, infrared light source unit 32, and infrared photodetector 30.

ATR prism 20 has a shape of a rectangular parallelepiped with missing parts. The cross-section of ATR prism 20 has a shape obtained by cutting two vertex angles from a rectangle at a certain angle. A shorter surface on which the vertex angles are cut as shown in FIG. 5 is brought into contact with living body surface 40 as a measuring surface. The angle of end face 20c of ATR prism 20 is set such that propagating infrared light 11b in ATR prism 20 is totally reflected at end faces 20a and 20b of ATR prism 20. The angle of end face 20d of ATR prism 20 is set such that radiated infrared light 11c perpendicularly enters infrared photodetector 30.

Antireflection coating is applied to end face 20c on which incident infrared light 11a from infrared light source unit 32 is incident and end face 20d from which radiated infrared light 11c exits toward infrared photodetector 30. Alternatively, incident infrared light 11a from infrared light source unit 32 may be made p-polarized light (polarized light is parallel to substrate 50), and end surface 20c, which is an incident surface, and end surface 20d, which is an exit surface, may be chipped to make an angle of incidence/exit a Brewster's angle.

The material for ATR prism 20 may be a single crystal of zinc sulfide (ZnS) which is transparent in a mid-infrared range and has a relatively low refractive index. The material for ATR prism 20 is not limited to the single crystal of zinc sulfide (ZnS) and may be a known material such as zinc selenide (ZnSe). End surface 20a of ATR prism 20 which comes into contact with the skin is coated with a thin film of, for example, SiO2 or SiN to cause no harm to a human body.

In Embodiment 2, for example, a quantum cascade laser module is used as infrared light source unit 32. The quantum cascade laser, which includes a single light source and has a high output and a high signal-to-noise ratio (SN ratio), is capable of high-accuracy measurements. A lens for collimating a beam is mounted in the quantum cascade laser module. The quantum cascade laser radiates infrared light in entirety or part of the wavelength region in the wavelength range of 8.5 µm to 10 µm, in which the wavelengths of a fingerprint spectrum of sugar are present.

In order to improve accuracy of measurement, a wavelength tunable laser can be used for measurements at a plurality of wavelengths. The wavelength tunable laser, however, is implemented as an external resonator, leading to large size and high cost due to complicated structure.

Figure 6:
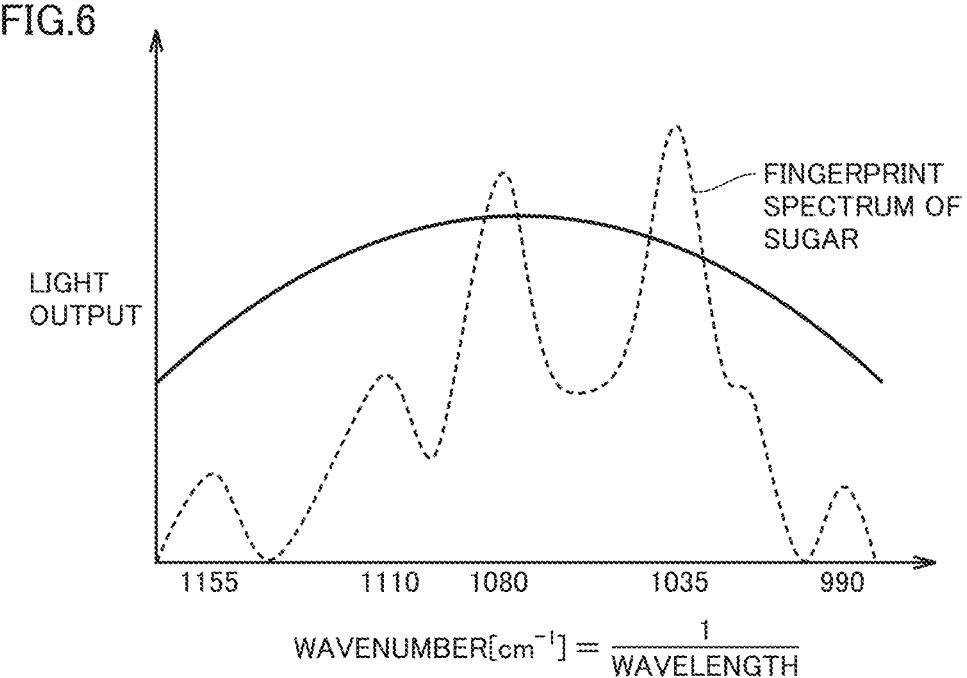
FIG. 6 shows a spectrum of light output from an infrared light source unit 32 of Embodiment 2.

FIG. 6 shows a spectrum of light output from infrared light source unit 32 of Embodiment 2.

Infrared light source unit 32 radiates infrared light in entirety or part of the wavelength region in the wavelength range of 8.5 µm to 10 µm, which includes the wavelengths of a fingerprint spectrum of sugar as shown in FIG. 6. Specifically, a wideband quantum cascade laser, not a wavelength tunable laser, is used as infrared light source unit 32 as described above.

In place of the wideband quantum cascade laser, infrared light source unit 32 may be a thermal light source of such a type that flows current through a filament for heating. In this case, temperature can be controlled by an amount of a current applied, and accordingly, wideband infrared rays according to black body radiation are radiated.

Alternatively, infrared light source unit 32 may not be a filament and may be a plasmon or a metamaterial light source that has a periodic pattern provided in a heating portion. In this case, infrared light source unit 32 is a high-efficiency light source because the radiation wavelength range is defined by surface structure and accordingly has reduced unnecessary radiation.

FIG. 6 shows the fingerprint spectrum of sugar, shown in FIG. 4, by a dotted line for comparison. Amplified spontaneous emission is used as the light over a wide wavelength region as shown in FIG. 6. This eliminates the need for using an expensive wavelength tunable laser as infrared light source unit 32, so that a small-size, low-cost light source can be used as infrared light source unit 32.

Light of at least one wavelength which is included in infrared light 11c radiated from ATR prism 20 is detected by infrared photodetector 30. This enables measurement of an amount of at least one biological material corresponding to at least one absorption wavelength. Plasmon resonance occurs in the surface of the light receiving portion of infrared photodetector 30, so that infrared light of at least one wavelength is absorbed. At least one of the absorbed wavelengths corresponds to the absorption wavelength of a biological material.

Figure 7:
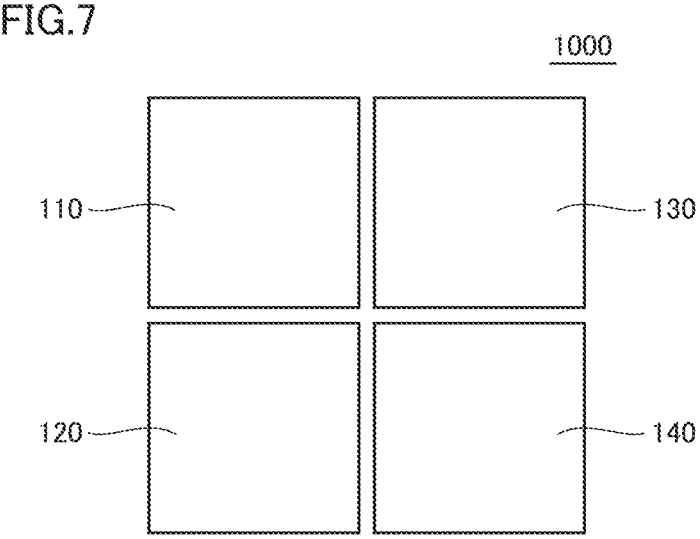
FIG. 7 is a schematic view of a sensor array 1000 of an infrared photodetector 30.

FIG. 7 is a schematic view of a sensor array 1000 of infrared photodetector 30. Sensor array 1000 is formed of non-cooling infrared sensors (hereinafter, also referred to as sensor pixels) 110, 120, 130, and 140 each detecting light having a different wavelength.

Sensor pixels 110, 120, 130, and 140 each include, for example, a wavelength-selective absorber using plasmon resonance in the surface of the light receiving portion. Such a structure can detect infrared light of the selected wavelength. The use of infrared photodetector 30 including an array of non-cooling infrared sensors which detect only the infrared light of the selected wavelength allows simultaneous measurements of a plurality of wavelengths, enabling a measurement in a short period of time.

As described below, the use of plasmon resonance eliminates the need for a spectral filter, simplifying the configuration of infrared photodetector 30, which leads to lower cost. Although wavelength selectivity decreases due to the thermal radiation of the spectral filter per se in an infrared wavelength range, the use of a plasmon structure, not the spectral filter, improves wavelength selectivity. This leads to higher sensitivity for detecting a trace amount of component, such as analysis of a blood sugar level.

When the quantum cascade laser and plasmon are used simultaneously, the selectivity of measurement wavelength is secured, and accordingly, black-body radiation components of other than the absorption peak wavelength of glucose can be removed. This leads to an improved SN ratio. Also, since a quantum cascade laser does not always need to be used for a reference wavelength, a broad light source and a plasmon enable selection of wavelengths. This leads to lower cost.

Further, when a diffraction grating is installed, wavelength resolution needs to be increased, and thus, the infrared photodetector and the diffraction grating need to be disposed apart from each other. However, the use of a plasmon as the light receiving portion eliminates the need for optical components such as a diffraction grating and a mirror. This can reduce the size of a biological material measuring apparatus.

The wavelengths for use in measurements are, for example, $\lambda 1$, $\lambda 2$, $\lambda 3$, and $\lambda 4$ in the wavelength range of 8.5 µm to 10 82 m in which the fingerprint spectrum of sugar is present. As described above, radiated infrared light 11c radiated from infrared light source unit 32 passes through ATR prism 20 while repeating total reflection. At that time, light of each of wavelengths λ1, λ2, and λ3 is absorbed by sugar in a human body, and the intensity of the light attenuates before reaching infrared photodetector 30. Thus, when the light of each of wavelengths λ1, λ2, and λ3 is measurable by infrared photodetector 30, the blood sugar level in a human body can be measured. Also, infrared light of wavelength λ4, which is not absorbed by sugar, is used as a reference wavelength.

Sensor pixels 110, 120, 130, and 140 of infrared photodetector 30 detect infrared light of wavelengths λ1, λ2, λ3, and λ4.

The infrared light of each of wavelengths λ1, λ2, λ3 is absorbed by sugar, as well as by water and any other biological material. On the other hand, the infrared light of wavelength λ4 is not absorbed by sugar but is absorbed by water and any other biological material. Thus, the intensity of the detected infrared light of each of the wavelengths λ1, λ2, and λ3 is corrected with the intensity of infrared light of wavelength λ4, leading to improved accuracy of measurement.

The infrared rays radiated from an external background and a human body may enter infrared photodetector 30. Wavelengths λ1, λ2, and λ3 can be set to values extremely close to each other, thereby making the effects of the infrared rays radiated from the background and the human body almost equal to each other, thus minimizing the effects of noise.

In order to eliminate such noise, radiated infrared light 11c may be chopped at a specific frequency using a chopper. Infrared light source unit 32 itself can be pulse-driven, and infrared light can be chopped using the frequency thereof to increase detection sensitivity. The signals output from sensor pixels 110, 120, 130, and 140 may be subjected to Fourier transform at a chopping frequency to obtain an output with noise reduced.

It suffices that a sensor pixel may be added in order to increase wavelengths to be detected. When a detection wavelength can be adjusted by controlling only the surface periodic structure of a sensor pixel, as many wavelengths as the pixels formed into an array can be detected.

Next, a specific example of infrared photodetector 30 will be described.

The modes of non-cooling infrared sensors (thermal infrared sensors) for use in the sensor pixels of infrared photodetector 30 include pyroelectric sensors, bolometers, thermopiles, and silicon on insulator (SOI) diodes. Even for different modes, plasmon resonance can be used for the light receiving portion of the sensor, that is, an absorber to enable the selection of wavelengths. The present embodiment can thus use not only the mode of non-cooling infrared sensor but also any mode as the mode of detecting infrared photodetector 30.

Figure 8:
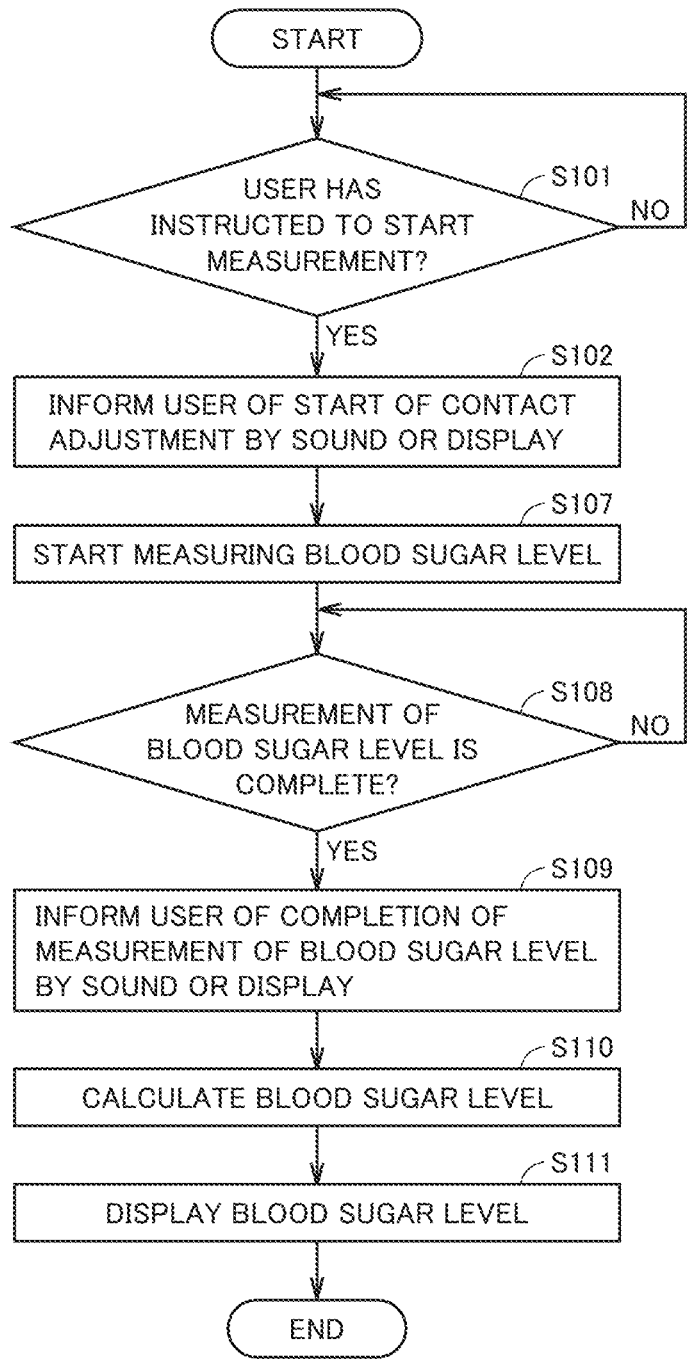
FIG. 8 is a flowchart showing an operational procedure of non-invasive biological material measuring apparatus 80 of Embodiment 2.

FIG. 8 is a flowchart showing an operational procedure of non-invasive biological material measuring apparatus 80 of Embodiment 2.

At S101, controller 52 determines whether a user has instructed to start measurement via keyboard 503. When the user has instructed to start measurement, the process proceeds to step S102.

At step S102, controller 52 outputs a message voice "measurement to be started" through speaker 504, thereby informing the user of a start of measurement of a blood sugar level.

At step S107, controller 52 starts measuring a blood sugar level.

At step S108, controller 52 determines whether the measurement of a blood sugar level is complete. When the measurement is complete, the process proceeds to step S109.

At step S109, controller 52 outputs a message voice "measurement complete" through speaker 504.

At step S110, controller 52 calculates a blood sugar level based on the measured intensity of infrared light.

At step S111, controller 52 displays the calculated blood sugar level on display 501.

[Notes]

The biological material measuring apparatus (80) of Embodiment 2 has the following features.

(5) A biological material measuring apparatus (80) includes an ATR prism (20) adherable to a living body surface (40), an infrared light source unit (32) to radiate, to the ATR prism (20), infrared light in entirety or part of a wavelength region including absorption wavelengths of a biological material, and an infrared photodetector (30) to detect infrared light of at least one wavelength which is emitted from the ATR prism (20).

Such a configuration can measure an amount of at least one biological material corresponding to at least one absorption wavelength.

(6) The infrared light source unit (32) comprises a single light source to radiate infrared light in a wavelength region detectable by the infrared photodetector (30).

Such a configuration can intensify infrared light and increase the SN ratio, enabling high-accuracy measurement.

(7) Infrared light of one or more wavelengths is absorbed upon generation of plasmon resonance in a surface of a light receiving portion of the infrared photodetector (30), and at least one of the one or more wavelengths corresponds to an absorption wavelength of the biological material.

Such a configuration can detect infrared light of the selected wavelength, enabling measurement of an amount of a biological material that absorbs the selected wavelength.

Embodiment 3

Differences from Embodiment 2 will be described.

Figure 9:
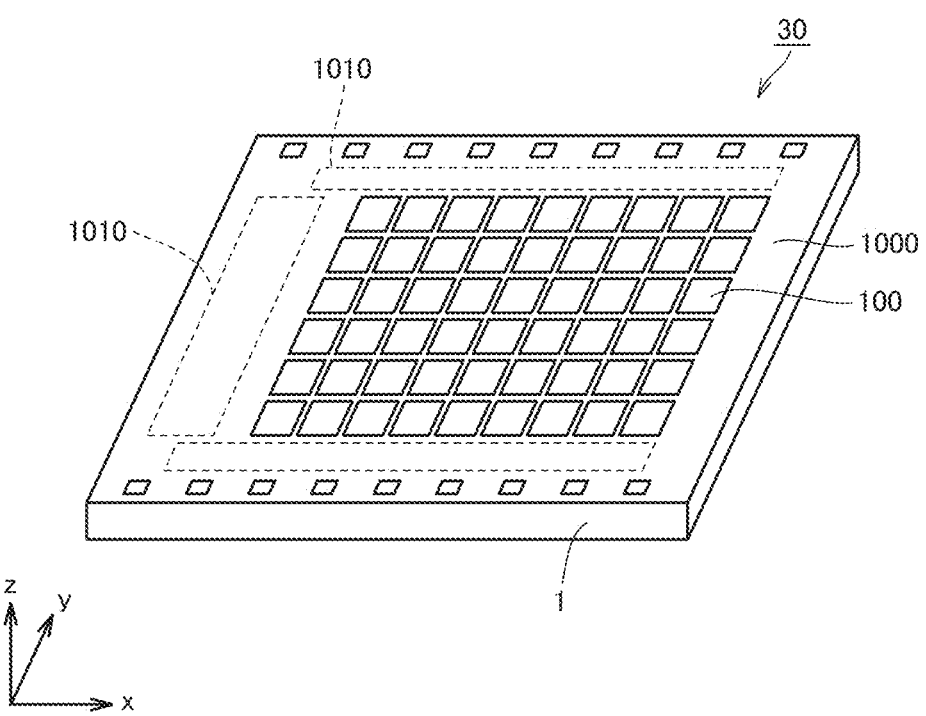
FIG. 9 shows a configuration of an infrared photodetector 30 of Embodiment 3.

FIG. 9 shows a configuration of an infrared photodetector 30 of Embodiment 3.

Infrared photodetector 30 is an integrated wavelength-selective infrared sensor. Infrared photodetector 30 includes a sensor array 1000 and a detection circuit 1010.

Sensor array 1000 includes 9×6 pixels (semiconductor optical devices) 100 arranged in rows and columns. On substrate 1, 9×6 semiconductor optical devices 100 are arranged in matrix (in array) in the X-axis and Y-axis directions. Light enters from the direction parallel to the Z-axis. That is to say, infrared photodetector 30 perpendicularly receives infrared light emitted from ATR prism 20.

Detection circuit 1010 is provided around sensor array 1000. Detection circuit 1010 processes a signal detected by semiconductor optical device 100 to detect an image. When the detected wavelengths are fewer, detection circuit 1010 is not required to detect an image and is merely required to detect an output from each device.

Description will be given below by taking a thermal infrared sensor as an example of semiconductor optical device 100.

Figure 10:
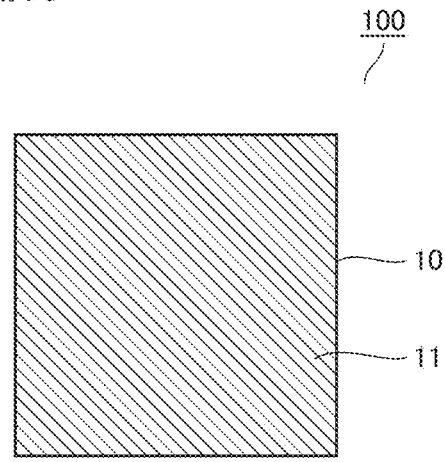
FIG. 10 is a top view of a semiconductor optical device 100 of Embodiment 3.

FIG. 10 is a top view of semiconductor optical device 100 of Embodiment 3. As shown in FIG. 10, semiconductor optical device 100 includes an absorber 10 serving as a light receiving portion.

Figure 11:
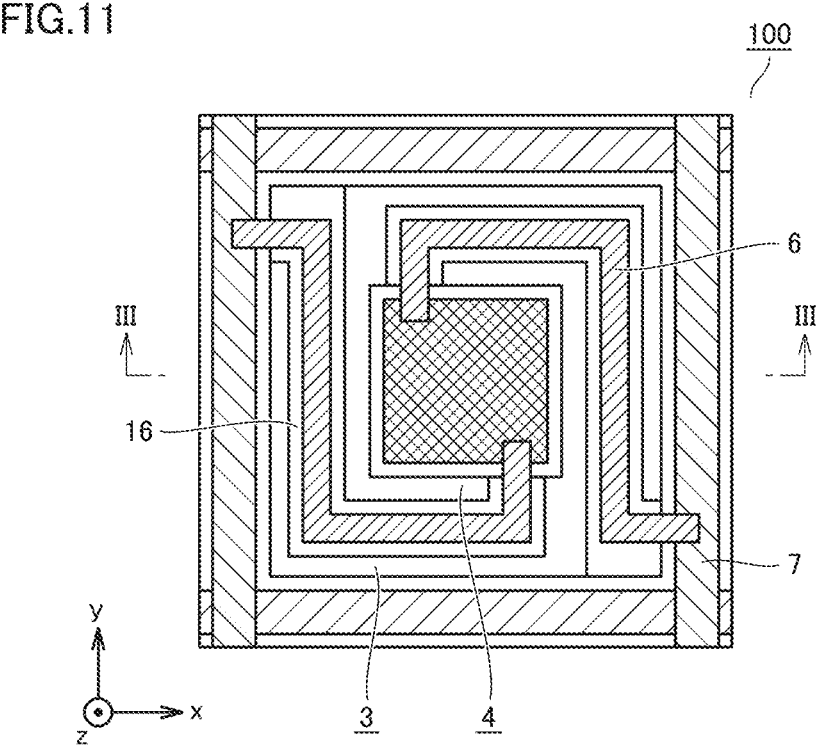
FIG. 11 is a top view of semiconductor optical device 100 of Embodiment 3 excluding an absorber 10.
Figure 12:
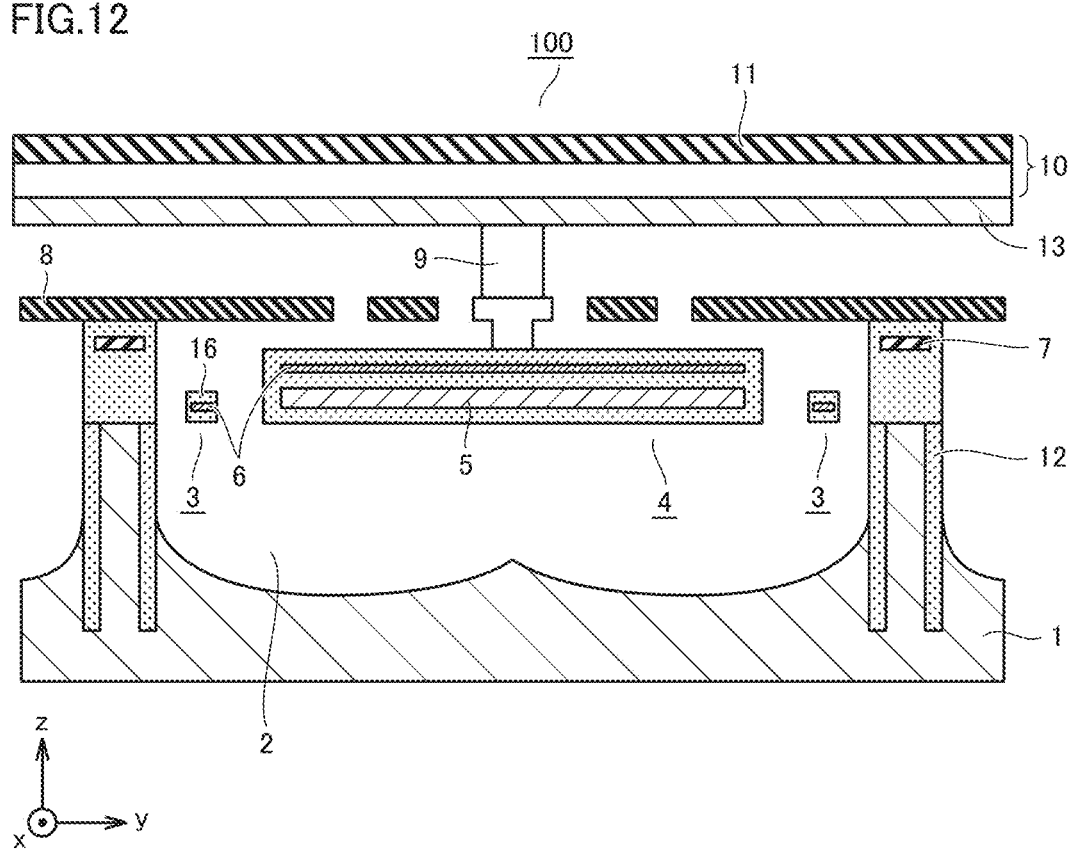
FIG. 12 is a sectional view of semiconductor optical device 100 of FIG. 11 (including absorber 10 and the like), as seen in the direction.
Figure 13:
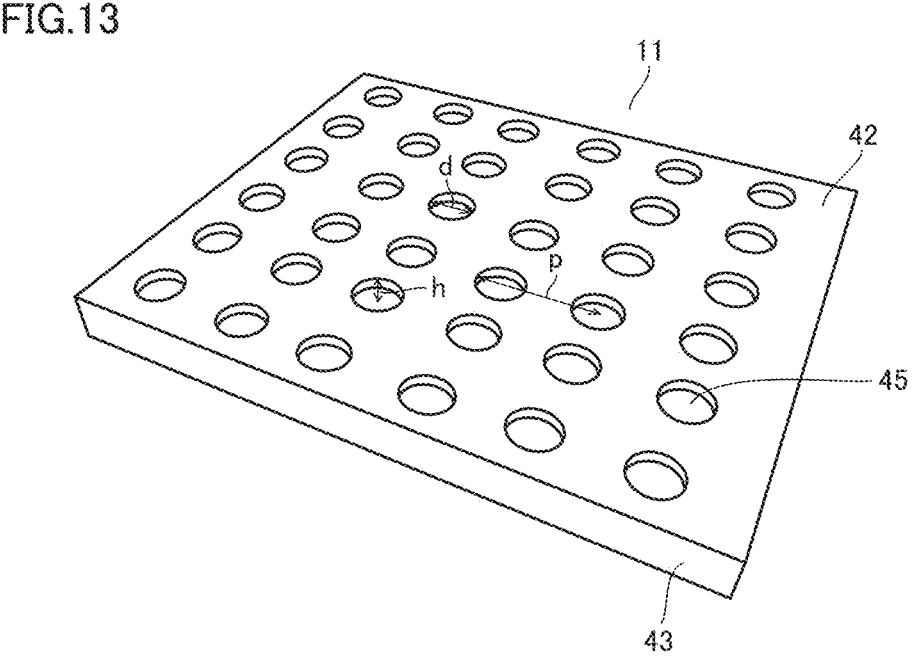
FIG. 13 shows absorber 10 of semiconductor optical device 100 of Embodiment 3.

FIG. 11 is a top view of semiconductor optical device 100 of Embodiment 3 excluding absorber 10. FIG. 11 does not show a protective film and a reflection film on a wire for clarification. FIG. 12 is a sectional view of semiconductor optical device 100 of FIG. 11 (including absorber 10 and the like), as seen in the direction. FIG. 13 shows absorber 10 of semiconductor optical device 100 of Embodiment 3.

As shown in FIG. 12, semiconductor optical device 100 includes, for example, a substrate 1 made of silicon. A hollow 2 is provided in substrate 1. A temperature detection unit 4, which detects temperatures, is disposed above hollow 2. Temperature detection unit 4 is supported by two support legs 3. As shown in FIG. 11, support leg 3 has a bridge shape bent in an L-shape as seen from above. Support leg 3 includes a thin metal wire 6 and a dielectric film 16 supporting thin metal wire 6.

Temperature detection unit 4 includes a detection film 5 and thin metal wire 6. Detection film 5 is formed of, for example, a diode containing crystal silicon. Thin metal wire 6 is also provided in support leg 3 and electrically connects an aluminum wire 7 and detection film 5, which are covered with an insulating film 12, to each other. Thin metal wire 6 is made of, for example, titanium alloy having a thickness of 100 nm. An electric signal output from detection film 5 is transmitted to aluminum wire 7 through thin metal wire 6 formed in support leg 3 and is extracted by detection circuit 1010 of FIG. 9. An electrical connection between thin metal wire 6 and detection film 5 and an electrical connection between thin metal wire 6 and aluminum wire 7 may be provided via a conductor (not shown) extending thereabove or therebelow if necessary.

A reflective film 8, which reflects infrared rays, is disposed to cover hollow 2; however, it is disposed to cover at least part of support leg 3 with reflective film 8 and temperature detection unit 4 not being thermally connected to each other.

As shown in FIG. 12, a support pillar 9 is provided above temperature detection unit 4. Absorber 10 is supported on support pillar 9. That is to say, absorber 10 is connected to temperature detection unit 4 by support pillar 9. Since absorber 10 is thermally connected to temperature detection unit 4, a change in the temperature generated in absorber 10 is conveyed to temperature detection unit 4.

At the same time, absorber 10 is disposed above reflective film 8 while it is not thermally connected with reflective film 8. Absorber 10 extends laterally in a plate shape so as to cover at least part of reflective film 8. As semiconductor optical device 100 is seen from above, thus, only absorber 10 is seen as shown in FIG. 10. Alternatively, absorber 10 may be formed directly above temperature detection unit 4.

In the present embodiment, a wavelength selection structure 11, which selectively absorbs the light of a certain wavelength, is provided in the surface of absorber 10 as shown in FIG. 12. An anti-absorption film 13, which prevents light absorption from the rear surface, is provided on the rear surface of absorber 10, that is, on the support pillar 9 side. This configuration allows absorber 10 to selectively absorb light of a specific wavelength. Since wavelength selection structure 11 may also absorb light, absorber 10 includes wavelength selection structure 11 in the present embodiment.

Next, description will be given of the structure in the case in which wavelength selection structure 11 uses surface plasmon. Providing a periodic structure made of metal in a light incidence surface causes surface plasmon at a wavelength corresponding to a surface periodic structure, so that light is absorbed. Thus, the surface of absorber 10 can be made of metal to control the wavelength selectivity of absorber 10 by the wavelength of incident light, an angle of incidence, and a periodic structure of the metal surface.

In the present embodiment, a phenomenon in which free electrons inside a metal film make a contribution and the generation of a surface mode by a periodic structure are regarded as being synonymous with each other in terms of absorption, and they are referred to as surface plasmon, surface plasmon resonance, resonance, pseudo-surface plasmon, or metamaterial without differentiating therebetween. The configuration of the present embodiment is also effective for light of a wavelength in a wavelength region of other than infrared light, for example, a visible light region, a near infrared region, and a THz region.

As shown in FIG. 13, wavelength selection structure 11 that selectively increases the absorption of light of a certain wavelength, which is provided in the surface of absorber 10, includes a metal film 42, a main body 43, and recesses 45.

The type of metal film 42 provided in the outermost surface of absorber 10 serving as the light receiving portion is selected from metals that easily cause surface plasmon resonance, such as Au, Ag, Cu, Al, Ni, and Mo. Alternatively, the type of metal film 42 may be a material that causes plasmon resonance, such as metallic nitrides including TiN, metallic borides, and metallic carbides. It suffices that metal film 42 in the outermost surface of absorber 10 has such a thickness as not to allow incident infrared light to pass therethrough. With such a film thickness, only surface plasmon resonance in the outermost surface of absorber 10 affects absorption and radiation of electromagnetic waves, and the material below metal film 42 does not optically affect absorption or the like.

A thickness (skin depth) $\lambda 1$ of a skin effect is represented by an expression below:

$$\delta 1 = (2/\mu\sigma\omega)^{1/2} \qquad (1)$$

where $\mu$ is a magnetic permeability of metal film 42, $\sigma$ is an electric conductivity of metal film 42, and $\omega$ is an angular frequency of incident light.

For example, when film thickness $\lambda$ of metal film 42 in the surface of absorber 10 is at least twice $\delta 1$, that is, from about several tens of nanometers to about several hundreds of nanometers, a leak of incident light to below absorber 10 can be made sufficiently small.

For example, in comparison of heat capacity between gold and oxide silicon (SiO2), oxide silicon has a smaller heat capacity. An absorber formed of main body 43 made of oxide silicon and the surface of metal film 42 made of gold can have a smaller heat capacity than an absorber made of gold alone, and accordingly, can have a higher response.

Next, a method of manufacturing absorber 10 will be described.

A periodic structure is formed on the front surface side of main body 43 formed of a dielectric or semiconductor by photolithography and dry etching, and then, metal film 42 is formed by sputtering or the like. Similarly for the rear surface, subsequently, a periodic structure is produced, and then, metal film 42 is formed.

Since the diameter of recess 45 is as small as about several micrometers, a manufacturing step is more simplified by forming metal film 42 after etching main body 43 to form recesses than by directly etching metal film 42 to form recesses. Since an expensive material, such as Au or Ag, is used for metal film 42, the use of main body 43 of dielectric or semiconductor can reduce the amount of metal used for reduced cost.

Next, the characteristics of absorber 10 will be described with reference to FIG. 13. Cylindrical recesses 45 each having a diameter d of 4 µm and a depth h of 1.5 82 m are arranged in tetragonal lattice with a period p of 8 µm. In this case, an absorption wavelength is about 8 µm. Alternatively, cylindrical recesses 45 each having a diameter d of 4 µm and a depth h of 1.5 µm are arranged in tetragonal lattice with a period p of 8.5 µm. In this case, an absorption wavelength is approximately 8.5 µm.

The relationship between the absorption wavelength and radiation wavelength of incident light and the period of recesses 45 is almost identical even when recesses 45 are arranged in tetragonal lattice or even when they are arranged in triangular lattice as long as absorber 10 has a two-dimensional periodic structure. That is to say, an absorption wavelength and a radiation wavelength are determined by the period of recesses 45. Considering reciprocal vectors of the periodic structure, theoretically, the absorption and radiation wavelengths are almost identical to the period in the tetragonal lattice arrangement, whereas the absorption and radiation wavelengths are a period $x\sqrt{3}/2$ in the triangular lattice arrangement. In actuality, however, the absorption and radiation wavelengths vary slightly depending on diameter d of recess 45. It is thus conceivable that incident light may be absorbed or radiated at a wavelength almost identical to a period in both the periodic structures.

The wavelength of infrared light to be absorbed can thus be controlled by the period of recesses 45. Generally, diameter d of recess 45 is desirably not less than a half of period p. If diameter d of recess 45 is smaller than a half of period p, a resonance effect tends to be smaller to reduce an absorptivity. However, since resonance is three-dimensional resonance in recess 45, sufficient absorption may be achieved even when diameter d is smaller than a half of period p. The value of diameter d with respect to period p is accordingly designed individually as appropriate. What is important is that an absorption wavelength is controlled mainly by period p. When diameter d is not less than a certain value with respect to period p, absorber 10 has sufficient absorption characteristics, providing ranges to design. Meanwhile, referring to a general expression of dispersion relation of surface plasmon, the light to be absorbed is irrelevant to depth h of recess 45 and depends on period p alone. The absorption wavelength and radiation wavelength thus do not depend on depth h of recess 45 shown in FIG. 13.

Although the absorber having recesses 45 arranged periodically has been described above, similar effects can be achieved also with the structure having projections 45a arranged periodically.

The absorption by absorber 10 having such an irregular structure reaches its maximum in the case of normal incidence. When the angle of incidence on absorber 10 deviates from normal incidence, the absorption wavelength also changes. Infrared photodetector 30 is thus disposed such that infrared light emitted from ATR prism 20 is radiated perpendicularly to the surface of absorber 10 serving as the light receiving portion.

[Notes]

The biological material measuring apparatus (80) of Embodiment 3 has the following features.

(8) Recesses (45) or projections (45b) are periodically formed in the surface of the light receiving portion of the infrared photodetector (30), and an outermost surface of the light receiving portion is a material that causes surface plasmon resonance.

Such a configuration allows the infrared photodetector (30) to have wavelength selectivity.

(9) A period of the recesses (45) or the projections (45b) in the surface of the light receiving portion of the infrared photodetector (30) corresponds to an absorption wavelength of the biological material.

With such a configuration, a biological material to be measured can be changed by changing the period of the recesses (45) or projections (45b).

(10) The infrared light emitted from the ATR prism (20) perpendicularly enters the surface of the light receiving portion of the infrared photodetector (30).

Such a configuration can maximize the absorption of infrared light in the infrared photodetector (30).

Embodiment 4

Differences from Embodiment 3 will be described.

In Embodiment 4, a quantum cascade laser is used as infrared light source unit 32. The quantum cascade laser oscillates at one or more signal wavelengths in the wavelength range of 8.5 µm to 10 µm in which the fingerprint spectrum of sugar is present and at a reference wavelength deviated slightly from the above wavelength range.

A Peltier device for stabilizing a wavelength and a leans for collimating a beam are mounted in a quantum laser module of the present embodiment. The other components are similar to those of Embodiment 3, which will not be repeated.

In measurement of a blood sugar level, the radiation from living body surface 40 is detected as noise, leading to reduced accuracy of measurement.

In the present embodiment, wavelengths for use in the quantum cascade laser are set to appropriate ones, and infrared photodetector 30 is used to remove a radiation spectrum from a living body. This enables high-accuracy measurement excluding radiation from a living body.

Embodiment 5

Differences from Embodiment 2 will be described.

Figure 14:
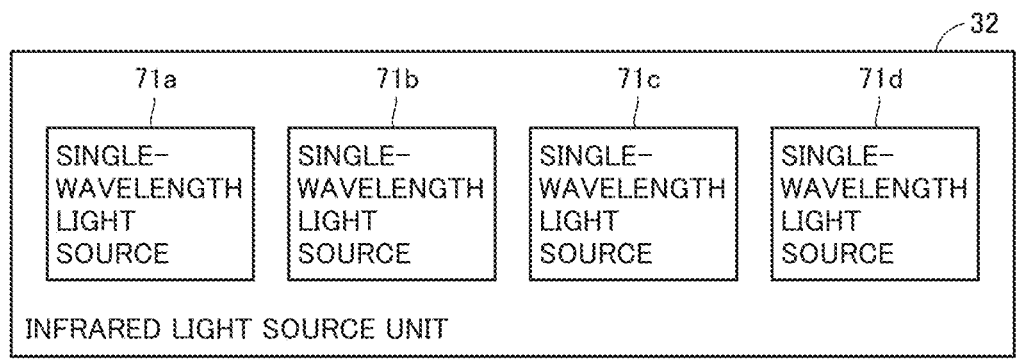
FIG. 14 shows a configuration of an infrared light source unit 32 of Embodiment 5.
Figure 15:
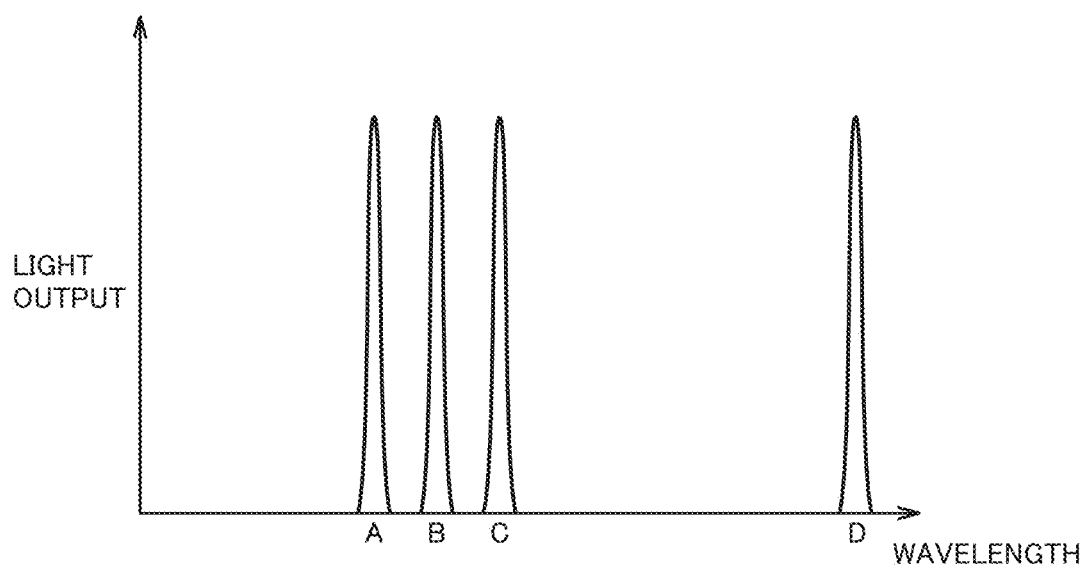
FIG. 15 shows a spectrum of light output from infrared light source unit 32 of Embodiment 5.

FIG. 14 shows a configuration of an infrared light source unit 32 of Embodiment 5. FIG. 15 shows a spectrum of light output from infrared light source unit 32 of Embodiment 5.

Infrared light source unit 32 includes single-wavelength light sources 71a, 71b, 71c, and 71d. Single-wavelength light sources 71a, 71b, 71c, and 71d output infrared light of single wavelengths A, B, C, and D, respectively, as shown in FIG. 15. Single wavelengths A, B, C, and D are included in the wavelength region that can be detected by infrared photodetector 30.

In the present embodiment, infrared photodetector 30 does not detect a radiation spectrum from a living body but can detect infrared light of wavelengths in a wide range (i.e., does not have wavelength selectivity).

For example, single-wavelength light sources 71a, 71b, 71c, and 71d can output infrared light at different timings, and infrared photodetector 30 that has no wavelength selectivity can receive infrared light of each single-wavelength light source.

[Notes]

The biological material measuring apparatus (80) of Embodiment 5 has the following features.

(11) A biological material measuring apparatus (80) includes an ATR prism (20) adherable to a living body surface (40), an infrared light source unit (32) to radiate, to the ATR prism, infrared light in entirety or part of a wavelength region including absorption wavelengths of a biological material, and an infrared photodetector (30) to detect infrared light emitted from the ATR prism (20). The infrared light source unit (32) comprises a plurality of light sources (71a, 71b, 71c, 71d), each of which radiates infrared light of a single wavelength included in a wavelength region detectable by the infrared photodetector (32).

Such a configuration allows the infrared photodetector (30) that does not have wavelength selectivity to receive infrared light from a plurality of light sources when the plurality of light sources output infrared light at different timings.

Embodiment 6

Differences from Embodiment 2 will be described.

Figure 16:
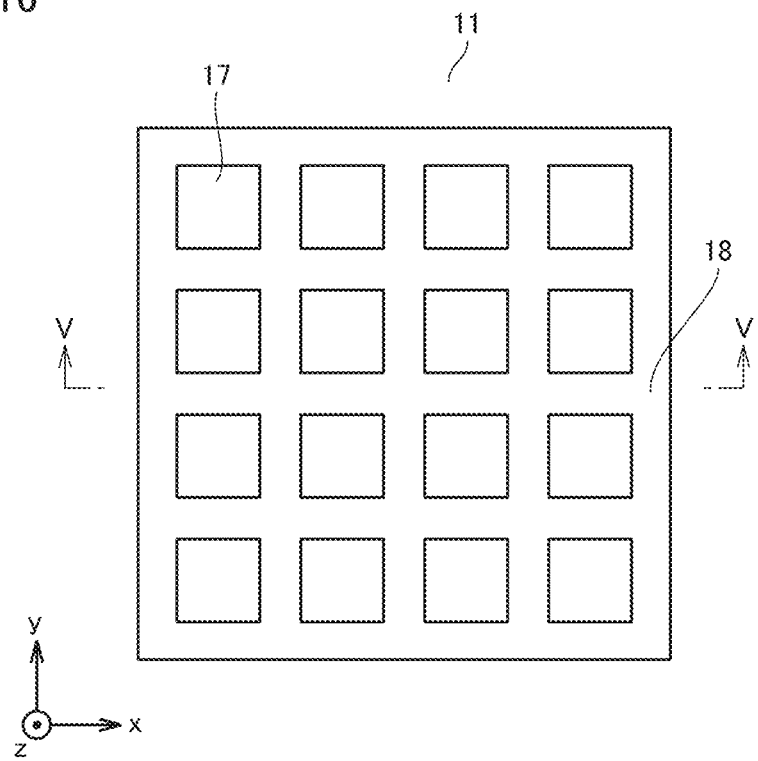
FIG. 16 is a top view of a wavelength selection structure 11 of Embodiment 6.
Figure 17:
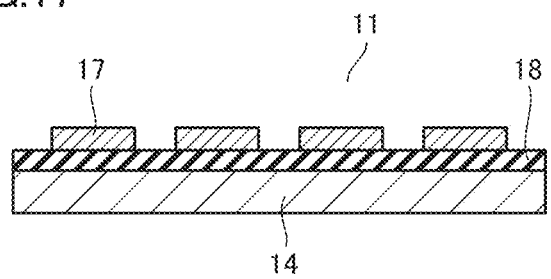
FIG. 17 is a sectional view of wavelength selection structure 11 of FIG. 16, as seen in the V-V direction.

FIG. 16 is a top view of a wavelength selection structure 11 of Embodiment 6. FIG. 17 is a sectional view of wavelength selection structure 11 of FIG. 16, as seen in the V-V direction.

Wavelength selection structure 11 includes a metal layer 14, an intermediate layer 18 on metal layer 14, and metal patches 17 on intermediate layer 18.

Metal layer 14 is made of, for example, aluminum, gold, or the like.

Intermediate layer 18 is formed of an insulator such as oxide silicon, a dielectric, or a semiconductor such as silicon or germanium. The selection of the material for intermediate layer 18 can control wavelengths to be detected, the number of wavelengths to be detected, and the band of wavelengths to be detected.

Metal patch 17 is formed of, for example, a metal such as gold, silver, or aluminum, or of graphene other than metal. When metal patch 17 is made of graphene, a film thickness can be reduced down to one atomic layer. This reduces a thermal time constant, enabling a high-speed operation. Alternatively, the material for metal patch 17 may be a material that causes surface plasmon resonance as described above.

The wavelength at which plasmon resonance occurs can be controlled by the size of metal patch 17 (the dimensions in the x and y directions of FIG. 16). Thus, changing the size of metal patch 17 allows the selection of an absorption wavelength. The size of metal patch 17 can accordingly be determined such that the wavelength absorbed by absorber 10 matches the absorption wavelength of a biological material to be measured. As shown in FIG. 16, in one example in which metal patch 17 has a square shape, an absorption wavelength is about 7.5 µm when the length of one side is 3 µm, and an absorption wavelength is about 8.8 µm when the length of one side is 3.5 µm. In this case, the period of metal patches 17 is determined to be larger than the absorption wavelength and larger than one side of metal patch 17. Consequently, the period of metal patches 17 has almost no effect on the absorption wavelength.

The use of the absorber of the present embodiment can reduce the size of a pixel, reducing the area of infrared photodetector 30 when the pixels are formed into an array.

The absorption structure of wavelength selection structure 11 of the present embodiment has no independence on an angle of incidence, and the absorption wavelength does not change even when an angle of incidence is changed. Similarly, when metal patch 17 has a symmetrical shape and a two-dimensional periodic structure, the absorption structure has no polarization independence. Thus, a permissible range is extended for the angle at which infrared photodetector 30 is installed. For a mobile biological material measuring apparatus, since a deviation of infrared photodetector 30 is feared, the use of the absorption structure of the present embodiment has a remarkable effect of good portability.

Although metal patches 17 are arranged with regular periods in matrix (two-dimensionally) in FIG. 16, they may be arranged one-dimensionally. Although polarization dependence occurs in this case, stray light can be eliminated by matching the direction of arrangement with the polarization of infrared light source unit 32. An SN ratio can thus be improved, enabling higher-accuracy measurement of a blood sugar level.

[Notes]

The biological material measuring apparatus (80) of Embodiment 6 has the following features.

(12) The surface of the light receiving portion of the infrared photodetector (30) is formed of a thin metal layer (14), an intermediate layer (18), and metal patches (17) stacked in order from inside, and an absorption wavelength of the biological material is controllable in accordance with a size of each of the metal patches (17).

With such a configuration, a biological material to be measured can be changed by changing the size of each of the metal patches (17).

(13) A period at which the metal patches (17) are arranged is larger than the absorption wavelength of the biological material and is larger than one side of each of the metal patches (17).

With such a configuration, the period of metal patches (17) has almost no effect on an absorption wavelength.

It is to be understood that the embodiments disclosed herein are presented for the purpose of illustration and non-restrictive in every respect. It is therefore intended that the scope of the present invention is defined by claims, not only by the embodiments described above, and encompasses all modifications and variations equivalent in meaning and scope to the claims.

REFERENCE SIGNS LIST 1, 50 substrate, 2 hollow, 3 support leg, 4 temperature detection unit, 5 detection film, 6 thin metal wire, 7 aluminum wire, 8 reflective film, 9 support film, 10 absorber, 11 wavelength selection structure, 11a incident infrared light, 11b propagating infrared light, 11c radiated infrared light, 12 insulating film, 13 anti-absorption film, 14 metal layer, 16 dielectric film, 17 metal patch, 18 intermediate layer, 20 ATR prism, 20a, 20b, 20c, 20d ATR prism end face, 30 infrared photodetector, 32 infrared light source unit, 40 living body surface, 42 metal film, 43 main body, 45 recess, 52, 250 controller, 54 user interface, 71a, 71b, 71c, 71d single-wavelength light source, 80 biological material measuring apparatus, 100 semiconductor device, 110, 120, 130, 140 non-cooling infrared sensor, 1000 sensor array, 1010 detection circuit, 200 light source, 210 prism, 220 light position detector, 230 prism, 230a incident light, 230b radiated light, 230c radiated and refracted light, 240 refractive index gradient.

The invention claimed is:

1. A biological. material measuring apparatus comprising:
an infrared light source configured to radiate infrared light in entirety or part of a wavelength region including absorption wavelengths of a biological material;
a prism configured to cause the infrared light radiated from the infrared light source to pass therethrough and emit the infrared light to a living body surface while being in contact with the living body surface;
a light source to radiate light of a wavelength in a visible light region or a near infrared region to the prism; and a light position detector to detect a path of light from the light source by detecting whether light from the light source which is emitted from the prism includes refracted light.

2. The biological material measuring apparatus according to claim 1, wherein the infrared light emitted to the living body surface is absorbed by the biological material present in the living body surface, and the absorption generates absorption heat to form a refractive index gradient in the prism.

3. The biological material measuring apparatus according to claim 2, wherein the light radiated from the light source passes through the refractive index gradient formed in the prism due to the absorption heat of the biological material.

4. The biological material measuring apparatus according to claim 3, comprising a controller to measure an amount of the biological material based on a difference between a position of incidence of light radiated from the light source which is detected by the light position detector when the infrared light source unit does not radiate the infrared light and a position of incidence of light radiated from the light source which is detected by the light position detector when the infrared light source radiates the infrared light.

5. The biological material measuring apparatus according to claim 1, wherein the light position detector includes a photodetector, and the light position detector detects the path of the light from the light source by detecting a position at which the light emitted from the prism enters the photodetector.

6. The biological material measuring apparatus according to claim 1, wherein a change in a state of the prism causes a change in the path of the light from the light source.

7. A biological material measuring apparatus comprising:
an ATR prism adherable to a living body surface;
an infrared light source configured to radiate, to the ATR prism, infrared light in entirety or part of a wavelength region including absorption wavelengths of a biological material; and
an infrared photodetector to detect infrared light of at least one wavelength which is emitted from the ATR prism,
wherein infrared light of one or more wavelengths is a-isorbed upon generation of plasmon resonance in a surface of a light receiving portion of the infrared photodetector, and at least one of the one or more wavelengths corresponds to an absorption wavelength of the biological material.

8. The biological material measuring apparatus according to claim 7, wherein the infrared light source unit comprises a single light source to radiate infrared light in a wavelength region detectable by the infrared photodetector.

9. The biological material measuring apparatus according to claim 7, wherein recesses or projections are periodically formed in the surface of the light receiving portion of the infrared photodetector, and an outermost surface of the light receiving portion is a material that causes surface plasmon resonance.

10. The biological material measuring apparatus according to claim 9, wherein a period of the recesses or the projections in the surface of the light receiving portion of the infrared photodetector corresponds to an absorption wavelength of the biological material.

11. The biological material measuring apparatus according to claim 10, wherein the infrared light emitted from the ATR prism perpendicularly enters the surface of the light receiving portion of the infrared photodetector.

12. The biological material measuring apparatus according to claim 10, wherein
the surface of the light receiving portion of the infrared photodetector is formed of a thin metal layer, an intermediate layer, and metal patches stacked in order from inside, and
an absorption wavelength of the biological material is controllable in accordance with a size of each of the metal patches.

13. The biological material measuring apparatus according to claim 12, wherein a period at which the metal patches are arranged is larger than the absorption wavelength of the biological material and is larger than one side of each of the metal patches.

14. A biological material measuring apparatus comprising:
an ATR prism adherable to a living body surface;
an infrared light source configured to radiate, to the ATR prism, infrared light in entirety or part of a wavelength region including absorption wavelengths of a biological material; and
an infrared photodetector to detect infrared light emitted from the ATR prism,
wherein the infrared light source comprises a plurality of light sources, each of which radiates infrared light of a single wavelength included in a wavelength region detectable by the infrared photodetector, and
infrared light of one or more wavelengths is absorbed upon generation of plasmon resonance in a surface of a light receiving portion of the infrared photodetector, and at least one of the one or more wavelengths corresponds to an absorption wavelength of the biological material.

* * * * *

UNITED STATES PATENT AND TRADEMARK OFFICE
CERTIFICATE OF CORRECTION

PATENT NO. : 11,832,942 B2
APPLICATION NO. : 16/962229
DATED : December 5, 2023
INVENTOR(S) : Kosuke Shinohara et al.

Page 1 of 1

It is certified that error appears in the above-identified patent and that said Letters Patent is hereby corrected as shown below:

In the Claims

Column 17, Line 20, delete "unit";

Column 17, Line 40-41, "a-isorbed" should be --absorbed--;

Column 17, Line 48, delete "unit".

Signed and Sealed this
Second Day of April, 2024

Katherine Kelly Vidal
*Director of the United States Patent and Trademark Office*